(12) United States Patent
Chaudry

(10) Patent No.: US 9,498,437 B2
(45) Date of Patent: Nov. 22, 2016

(54) INHALABLE FORMULATIONS FOR TREATING PULMONARY HYPERTENSION AND METHODS OF USING SAME

(75) Inventor: Imtiaz Chaudry, Napa, CA (US)

(73) Assignee: Mylan Specialty L.P., Basking Ridge, NJ (US)

( * ) Notice: Subject to any disclaimer, the term of this patent is extended or adjusted under 35 U.S.C. 154(b) by 0 days.

(21) Appl. No.: 11/316,458

(22) Filed: Dec. 22, 2005

(65) Prior Publication Data

US 2006/0104913 A1  May 18, 2006

Related U.S. Application Data

(63) Continuation of application No. PCT/EP2004/006629, filed on Jun. 18, 2004, which is a continuation of application No. 10/609,233, filed on Jun. 27, 2003.

(51) Int. Cl.
| | |
|---|---|
| *A61K 9/00* | (2006.01) |
| *A61K 31/00* | (2006.01) |
| *A61K 31/401* | (2006.01) |
| *A61K 31/404* | (2006.01) |
| *A61K 31/472* | (2006.01) |
| *A61K 31/55* | (2006.01) |
| *A61K 31/5575* | (2006.01) |
| *A61K 31/5585* | (2006.01) |
| *A61K 31/675* | (2006.01) |
| *A61K 38/55* | (2006.01) |
| *A61K 45/06* | (2006.01) |

(52) U.S. Cl.
CPC .......... *A61K 9/0078* (2013.01); *A61K 31/00* (2013.01); *A61K 31/401* (2013.01); *A61K 31/404* (2013.01); *A61K 31/472* (2013.01); *A61K 31/55* (2013.01); *A61K 31/5575* (2013.01); *A61K 31/5585* (2013.01); *A61K 31/675* (2013.01); *A61K 38/556* (2013.01); *A61K 45/06* (2013.01)

(58) Field of Classification Search
CPC .... A61K 9/0078; A61K 9/0073; A61K 9/08; A61K 9/12; A61K 9/4858; A61K 31/40; A61K 31/44; A61K 31/194; A61K 31/554; A61K 31/4965; A61K 31/00; A61K 31/401; A61K 31/404; A61K 31/472; A61K 31/55; A61K 31/5575; A61K 31/5585; A61K 31/675; A61K 38/556; A61K 45/06; C07D 207/00; C07D 211/00; C07D 213/00; C07D 241/02; C07D 281/06
USPC .............. 514/356, 183, 211.03, 252.12, 315, 514/351, 422, 929, 958; 424/78.1, 78.12, 424/78.23, 43, 45, 434
See application file for complete search history.

(56) References Cited

U.S. PATENT DOCUMENTS

| | | | |
|---|---|---|---|
| 2,414,918 A | 1/1947 | Abramson | |
| 4,374,829 A | 2/1983 | Harris | |
| D275,732 S | 10/1984 | Bauwens et al. | |
| D289,609 S | 5/1987 | Bauwens et al. | |
| D296,869 S | 7/1988 | Bauwens | |
| 4,885,305 A * | 12/1989 | Kiechel et al. | ............... 514/356 |
| D317,715 S | 6/1991 | Bauwens | |
| 5,376,666 A | 12/1994 | Duncia | |
| 5,554,610 A * | 9/1996 | Williams | ............... A61K 31/44 514/223.2 |
| 5,756,574 A | 5/1998 | Baumstark et al. | |
| 5,759,565 A | 6/1998 | Azria et al. | |
| 5,804,212 A | 9/1998 | Illum | |
| 5,873,359 A | 2/1999 | Zapol et al. | |
| 5,968,911 A | 10/1999 | Lawson et al. | |
| 5,980,882 A * | 11/1999 | Eichman | .......... A61K 47/48784 424/78.12 |
| 6,174,906 B1 | 1/2001 | Elliott et al. | |
| 6,187,765 B1 | 2/2001 | Harris et al. | |
| 6,197,762 B1 | 3/2001 | Garvey et al. | |
| 6,521,212 B1 | 2/2003 | Cloutier et al. | |
| 6,559,313 B2 | 5/2003 | Myers et al. | |
| 6,608,054 B2 | 8/2003 | Meade et al. | |
| 6,716,875 B1 | 4/2004 | Fossa | |
| 6,939,534 B2 | 9/2005 | Moskowitz | |
| 6,967,017 B1 * | 11/2005 | Malvolti | ............. A61K 9/0078 424/198.1 |
| RE39,072 E | 4/2006 | Adachi et al. | |
| 2001/0008632 A1 | 7/2001 | Freund et al. | |
| 2001/0031738 A1 * | 10/2001 | Schwarz | ............... C07K 16/24 514/44 A |

(Continued)

FOREIGN PATENT DOCUMENTS

| | | |
|---|---|---|
| AU | 2004251014 B2 | 11/2010 |
| CA | 2 530 632 C | 3/2012 |
| CN | 1822817 B | 10/2012 |
| EP | 0570260 A1 | 11/1993 |
| EP | 0 579 260 A1 | 1/1994 |

(Continued)

OTHER PUBLICATIONS

Brown, T. L. et al. Chemistry: The Central Science, 6th edition, Prentice Hall: Englewood Cliffs, NJ, 1994, pp. 112-113, 628-630, and 1016.*

(Continued)

*Primary Examiner* — Jane C Oswecki

(57) ABSTRACT

The present invention is directed to an inhalable formulation for the treatment of pulmonary hypertension in a mammal (e.g., humans), wherein the formulation comprises at least one hypertension reducing agent, including but not limited to an angiotensin converting enzyme inhibitor, angiotensin receptor blocker, beta-blocker, calcium-channel blocker or vasodilator, or any combination thereof. The formulations of the present invention may be a solution or suspension, and preferably are suitable for administration via nebulization. The present invention is also directed to a method and kit for treating a mammal suffering from pulmonary hypertension.

17 Claims, No Drawings

(56) References Cited

U.S. PATENT DOCUMENTS

| | | | |
|---|---|---|---|
| 2002/0090388 | A1 | 7/2002 | Humes et al. |
| 2002/0115655 | A1 | 8/2002 | Mehanna et al. |
| 2002/0132787 | A1 | 9/2002 | Eljamal et al. |
| 2002/0142970 | A1 | 10/2002 | Vaughan |
| 2002/0165249 | A1* | 11/2002 | Achari et al. ................. 514/289 |
| 2002/0183347 | A1 | 12/2002 | Meade et al. |
| 2003/0005924 | A1 | 1/2003 | Rabinowitz et al. |
| 2003/0005926 | A1 | 1/2003 | Jones et al. |
| 2003/0040509 | A1 | 2/2003 | Moskowitz |
| 2003/0062043 | A1 | 4/2003 | Fine et al. |
| 2003/0078190 | A1 | 4/2003 | Weinberg |
| 2003/0103983 | A1* | 6/2003 | Pressler ............... A61K 31/401 424/176.1 |
| 2004/0048905 | A1* | 3/2004 | Daley et al. ................... 514/355 |
| 2004/0242567 | A1 | 12/2004 | Cosnier-Pucheu et al. |
| 2004/0265238 | A1 | 12/2004 | Chaudry |
| 2004/0266685 | A1* | 12/2004 | Conrad et al. .................. 514/12 |
| 2004/0266869 | A1 | 12/2004 | Montague et al. |
| 2005/0119330 | A1* | 6/2005 | Kao ...................... A61K 31/255 514/423 |
| 2005/0191245 | A1* | 9/2005 | Adams et al. .................. 424/45 |
| 2006/0002992 | A1 | 1/2006 | Schmehl et al. |
| 2006/0258652 | A1* | 11/2006 | Haj-Yehia et al. ........ 514/230.5 |
| 2007/0117861 | A1* | 5/2007 | Wang et al. .................. 514/423 |
| 2007/0166240 | A1* | 7/2007 | Banerjee .............. A61K 9/0078 424/46 |

FOREIGN PATENT DOCUMENTS

| | | |
|---|---|---|
| EP | 0 630 887 A1 | 12/1994 |
| EP | 1 638 525 B1 | 3/2012 |
| GB | 1114313 | 5/1968 |
| JP | 1-100120 A | 4/1989 |
| JP | 5-506642 A | 9/1993 |
| JP | 07-053358 A | 2/1995 |
| JP | H07-53358 A | 2/1995 |
| JP | 09-512523 A | 12/1997 |
| JP | H10-500420 A | 1/1998 |
| JP | 2002-529393 A | 9/2002 |
| JP | 2002-539154 A | 11/2002 |
| JP | 2005-501573 A | 1/2005 |
| JP | 2005-503378 A | 2/2005 |
| JP | 2005-506369 A | 3/2005 |
| JP | 2011-172929 A * | 9/2011 |
| JP | 2011-201907 A | 10/2011 |
| RU | 2161483 | 1/2001 |
| RU | 2161485 C2 | 1/2001 |
| RU | 2 198 162 C2 | 2/2003 |
| WO | WO-91/10428 A1 | 7/1991 |
| WO | WO 93/04671 A | 3/1993 |
| WO | WO-96/10588 A1 | 4/1996 |
| WO | WO 95/31964 A1 | 3/1997 |
| WO | WO-97/27185 A1 | 7/1997 |
| WO | WO 00/00193 * | 1/2000 |
| WO | WO 00/27395 A1 | 5/2000 |
| WO | WO-00/34243 A1 | 6/2000 |
| WO | WO-01/54677 A2 | 8/2001 |
| WO | WO 01/93846 A | 12/2001 |
| WO | WO 01/95880 A1 | 12/2001 |
| WO | WO 02/15891 A2 | 2/2002 |
| WO | WO 02/36158 A1 | 5/2002 |
| WO | WO 02/47668 A2 | 6/2002 |
| WO | WO-02/055136 A2 | 7/2002 |
| WO | WO 02/094237 | 11/2002 |
| WO | WO 03/035062 | 1/2003 |
| WO | WO 03/013434 A2 | 2/2003 |
| WO | WO 03/094915 * | 11/2003 |

OTHER PUBLICATIONS

CRC Handbook of Chemistry and Physics, 75th, edition, Frederike, H. P. R. and Lide, D. R., Eds., CRC Press: Boca Raton, 1994-1995, pp. 7-30.*

Yang et al. "Inhaled nanoparticles—A current review," International Journal of Pharmaceutics, 2008, 356, pp. 239-247.*
Office Action for U.S. Appl. No. 13/020,429 dated Jul. 23, 2014.
Office Action for U.S. Appl. No. 13/020,429; dated Aug. 15, 2013.
Verlag, Editio Cantor, Rote Liste Service GmbH, "Rote Liste 2002, Pres i.v.1,25mg (27277), Xanef i.v. 1,25mg (27279)", 2002, *Rote Liste 2002*.
Written Opinion for PCT/EP2004/006629 dated Dec. 27, 2005.
Gomez, H. J., et al.; "*Enalapril: A Review of Human Pharmacology;*" Drugs, vol. 30, Suppl. 1; pp. 13-24; dated 1985.
Yoshida, H.; The Journal of Therapy, vol. 80, extra issue; pp. 196-197; dated 1998.
Yoshida, H.; Pharmacia, vol. 33, No. 4; pp. 376-381; dated 1997.
"*Encyclopedia of Pharmaceutical Additives 2000;*" vol. 38; dated 2000.
Office Action for Japanese Application No. 2006-516000; dated Jan. 7, 2014.
Fukuoka S, et al.; "*Influence of neural blockages and proglumide on rat pancreatic enzyme secretion in response to intraluminal fatty acid;*" Proceedings of the Society for Experimental Biology and Medicine, vol. 186; pp. 27-35; dated 1987; retrieved on May 26, 2006 from <http://www.ebmonline.org/cgi/content/abstact/186/1/27>.
McInnes, G, T.; "*Debate: Does it matter how you lower blood pressure?*" Curr Control Trials Cardiovasc Med, vol. 2; pp. 63-66;; dated 2001; retrieved on Apr. 4, 2014 from <http://www.ncbi.nlm.nih.gov/pmc/articles/PMC59626/>.
Seggewiss, H., et al.; "*Management of hypertrophic cardiomyopathy in children;*" Pediatric Drugs, vol. 5, No. 10; pp. 663-672; dated 2003; retrieved on May 31, 2006 from <http://www.ncbi.nlm.nih.gov/pubmed/14510624>.
"*Angiotensin II Receptor Blockers—Their role in hypertension and congestive heart failure;*" Therapeutics Letters, Issue 28; dated Jan./Feb./Mar. 1999; retrieved on Apr. 4, 2014 from <http://www.ti.ubc.ca/pages/letter28.htm>.
"*digoxin Index;*" MedicineNet.com; retrieved on May 31, 2006 from <http://www.medicinenet.com/digoxin/article.htm>.
"*Hypertension;*" DoctorsLounge; dated Sep. 19, 2006; retrieved on Apr. 9, 2014 from <http://www.doctorslounge.com/cardiology/diseases/hypertension_treatment.htm>.
"*Lanoxin;*" Drugs.com; retrieved on May 31, 2006 from <http://www.drugs.com/lanoxin.html>.
International Preliminary Report on Patentability for Application No. PCT/EP2004/006692; dated Jan. 3, 2006.
International Search Report for Application No. PCT/EP2004/006629; dated Mar. 18, 2005.
Office Action for Australian Application No. 2004251014; dated Mar. 12, 2009.
Office Action for Australian Application No. 2004251014; dated Feb. 17, 2010.
Office Action for Australian Application No. 2004251014; dated Aug. 17, 2010.
Office Action for Australian Application No. 2011200464; dated May 24, 2012.
Office Action for Australian Application No. 2011200464; dated Jul. 26, 2012.
Office Action for Chinese Application No. 200480020228.1; dated Nov. 9, 2007.
Office Action for Chinese Application No. 200480020228.1; dated Apr. 14, 2010.
Office Action for Chinese Application No. 200480020228.1; dated Sep. 22, 2011.
Office Action for Chinese Application No. 200480020228.1; dated Oct. 28, 2011.
Office Action for Chinese Application No. 200480020228.1; dated Jun. 28, 2012 (Notice of Grant).
Office Action for European Application No. 04740073.4; dated May 10, 2006.
Office Action for European Application No. 04740073.4; dated Aug. 7, 2006.
Office Action for European Application No. 04740073.4; dated Apr. 25, 2008.

(56) References Cited

OTHER PUBLICATIONS

Office Action for European Application No. 04740073.4; dated Dec. 16, 2008.
Office Action for European Application No. 04740073.4; dated Aug. 24, 2009.
Office Action for European Application No. 04740073.4; dated Sep. 23, 2011.
Office Action for European Application No. 04740073.4; dated Feb. 9, 2012.
Office Action for Hong Kong Application No. 06113768.8; dated Apr. 16, 2013 (Notification of Grant).
Office Action for Indonesian Application No. W-00200503508; dated Oct. 25, 2007.
Office Action for Indonesian Application No. W-00200503508; dated Jan. 11, 2012.
Office Action for Japanese Application No. 2006-516000; dated Sep. 8, 2010.
Office Action for Japanese Application No. 2006-516000; dated Apr. 6, 2011.
Office Action for Korean Application No. 2005-7025128; dated Mar. 16, 2012.
Office Action for Korean Application No. 2005-7025128; dated Aug. 16, 2012.
Office Action for Korean Application No. 2005-7025128; dated Dec. 20, 2013.
Office Action for Korean Application No. 2012-015386; dated Aug. 28, 2012.
Office Action for Pilipino Application No. 1-2005-502201; dated Oct. 16, 2008.
Office Action for Pilipino Application No. 1-2005-502201; dated Jun. 24, 2009.
Office Action for Pilipino Application No. 1-2005-502201; dated Oct. 28, 2009.
Office Action for Pilipino Application No. 1-2005-502201; dated Mar. 30, 2011.
Office Action for Pilipino Application No. 1-2005-502201; dated Jul. 12, 2011.
Office Action for Russian Application No. 2010152753/15; dated Jan. 17, 2013.
Office Action for Singaporean Application No. 200508316-7; dated Jul. 26, 2006.
Office Action for Singaporean Application No. 200508316-7; dated Mar. 15, 2007.
Office Action for Singaporean Application No. 200508316-7; dated Jan. 31, 2008.
Office Action for U.S. Appl. No. 10/609,233; dated Mar. 27, 2006.
Office Action for U.S. Appl. No. 10/609,233; dated Oct. 17, 2006.
Office Action for U.S. Appl. No. 10/609,233; dated Jun. 19, 2007.
Office Action for U.S. Appl. No. 10/609,233; dated Apr. 4, 2008.
Office Action for U.S. Appl. No. 10/609,233; dated Feb. 4, 2009.
Office Action for U.S. Appl. No. 10/609,233; dated Aug. 6, 2009.
Office Action for U.S. Appl. No. 10/609,233; dated Mar. 9, 2010.
Office Action for U.S. Appl. No. 10/609,233; dated Sep. 3, 2010.
Office Action for U.S. Appl. No. 13/020,429; dated Feb. 15, 2012.
Office Action for U.S. Appl. No. 13/020,429; dated Sep. 17, 2012.
Office Action for U.S. Appl. No. 13/020,429; dated Dec. 5, 2013.
Pretrial Examination Report for Japanese Application No. 2006-516000; dated Dec. 7, 2011.
"Sorbitan Trioleate ;" Chemical Book; dated 2010; retrieved on Mar. 20, 2014 from <http://www.chemicalbook.com/ChemicalProductProperty_EN_CB4677178.htm>.
Office Action for Russian Application No. 2010 152 753 dated Jul. 6, 2012 (5 pages).
Pretrial Examination Report for Japanese Application No. 2006-516000 dated Feb. 19, 2013.
Gong, F. et al., *Inhalation of Nebulized Nitroglycerin in Dogs with Experimental Pulmonary Hypertension Induced by U46619*, Pediatrics International (2000) 42, pp. 225-258.

Lotvall, J. O. et al., *Effects of Aerosolised Substance P on Lung Resistance in Guinea-Pigs: A Comparison Between Inhibition of Neutral Endopeptidase and Angiotensin-Converting Enzyme*, Br. J. Pharmacol, 1990, 100, pp. 69-72.
Ogiku, N. et al., *No Relation of the Suppressive Effect on the Sympathetic Nervous System to the Acute Hypotension Caused by Imidapril and Enalapril*, Japan. J. Pharmacol. 63 (1993) 295-303.
Sereda, V.P. et al., *Ingaljatsionnaja terapia hronicheskih obstrukivenyh zabolevanij legkih* [*Inhalation therapy of the chronic obstructive pulmonary diseases*]. Praktik, FARMindex, Issue 4, Feb. 2003 (1 page).
Verlag, Editio Cantor, Rote Liste Service GmbH, "Rote Liste 2002, Pres i.v.1,25 mg (27277), Xanef i.v. 1,25 mg (27279)", 2002, *Rote Liste 2002*; 2 pages.
Higenbottam, T. et al. (editors), "Inhalation Therapy for Pulmonary Hypertension", The Proceedings of a Symposium . . . The Respiratory Society, Berlin, Sep. 2001, p. 66.
*Cardiothoracic Anesthesia, Respiration and Airway, Inhaled Iloprost Controls Pulmonary Hypertension After Cardiopulmonary Bypass*, K. Theodoraki et al., Canadian Journal of Anesthesia, vol. 49, No. 9, Nov. 2002, pp. 963-967.
*The Effect of High Doses of Calcium-Channel Blockers on Survival in Primary Pulmonary Hypertension*, S. Rich et al., The New England Journal of Medicine, vol. 327, No. 2, Jul. 1992, pp. 76-81.
*Aerosolized Prostacyclin and Iloprost in Severe Pulmonary Hypertension*, H. Olschewski et al, Annals of Internal Medicine, American College of Physicians, May 1996; 124:820-824, available at http://www.acponline.org/journals/annals/01may96/iloprost.htm (Jun. 24, 2003), 6 pages.
*Iloprost Inhaled Prostacyclin*, Pulmonary Hypertension Treatment, available at http://www.pulmonary-hypertension-treatments.com/iloprost.html (Jun. 24, 2003), 2 pages.
*Beta-Blocker*, The Columbia Encyclopedia, Sixth Edition, 2001, available at http://www.bartleby.com/65/be/beta-b.html (May 21, 2003), 1 page.
*Beta Blockers for CHF*, R. Garg et al., Postgraduate Medicine on line, vol. 109, No. 3, Mar. 2001, available at http://www.postgradmed.com/issues/2001/03_01/garg.htm (May 21, 2003), 13 pages.
*Beta-adrenergic Blocking Agents (Systemic)*, provided by Thomson MICROMEDEX, Yahoo! Health, available at http://health.yahoo.com/health/drugs/202087/overview.html (May 21, 2003), 9 pages.
*Beta Blockers*, MedicineNet.com, available at http://www.medicinenet.com/Beta_Blockers/article.htm (May 23, 2003), 2 pages.
*What Atenolol Is*, available at http://www.sunderland.ac.uk/~hs0dad/profile/atenolol/what.htm (May 21, 2003), 4 pages.
*ACE Inhibitor*, The Columbia Encyclopedia, Sixth Edition, 2001, available at http://www.bartleby.com/65/ac/ACE-i.html (May 21, 2003), 2 pages.
*Diagnosis and Treatment of Pulmonary Hypertension*, T. D. Nauser et al., American Family Physician, May 1, 2001, available at http://www.aafp.org/afp/20010501/1789.html (May 19, 2003), 13 pages.
*What Is Pulmonary Hypertension*, PHA, available at http://www.phassociation.org/Lear/WhatisPH.htm (May 19, 2003), 2 pages.
*What Is PH*, PHA, available at http://www.phassociation.org/Lear/whatisPH.htm (Dec. 12, 2002), 2 pages.
*Calcium Channel Blockers (CCBs)*, O. Ogbru et al., MedicineNet.com, available at http://www.medicinenet.com/Calcium_Channel_Blockers/article.htm (May 23, 2003), 3 pages.
*Epoprostenol (Prostacyclin) and Pulmonary Hypertension*, Annals of Internal Medicine, vol. 132, No. 6, Mar. 2000, pp. 500-502.
*Remodulin (Treprostinil)*, CenterWatch, available at http://www.centerwatch.com/patient/drugs/dru785.html (May 20, 2003), 3 pages.
*Epoprostenol (Systemic)*, Medlineplus, available at http://www.nlm.nih.gov/medlineplus/druginfo/uspdi/203429.html (May 20, 2003), 6 pages.
*Enalaprilat Injection*, Bedford Laboratories, available at http://www.bedfordlabs.com/products/010-10.html (May 21, 2003), 1 page.

(56) References Cited

OTHER PUBLICATIONS

*Calcium-Channel Blockers*, Texas Heart Institute, available at http://www.tmc.edu/thi/calcmeds.html (May 21, 2003), 4 pages.
*Angiotensin-converting Enzyme Inhibitors*, healthAtoz, available at http://www.healthatoz.com/healthatoz/Atoz/ency/angiotensin-converting_enzyme_inhibito . . . (May 21, 2003), 7 pages.
*Prostaglandin*, NDI Foundation, available at http://www.ndif.org/Terms/prostaglandin.html (May 23, 2003), 1 page.
*Prostaglandin*, ansme.com, available at http://define.ansme.com/words/p/prostaglandin.html (May 23, 2003), 1 page.
*Eicosanoid*, available at http://www.kumc.edu/instruction/medicine/pathology/ed/keywords/kw_eicosano.html (May 23, 2003), 1 page.
*Prostaglandin*, available at http://www.kumc.edu/instruction/medicine/pathology/ed/keywords/kw_prostagl.html (May 23, 2003), 1 page.
*Prostacyclin*, available at http://www.kumc.edu/instruction/medicine/pathology/ed/keywords/kw_prostacy.html (May 23, 2003), 1 page.
*Treprostinil (Systemic)*, Medlineplus, available at http://www.nlm.nih.gov/medlineplus/druginfo/uspdi/500385.html (May 20, 2003), 4 pages.
*Inhalation of Nebulized Nitroglycerin in Dogs with Experimental Pulmonary Hypertension Induced by U46619*, F. Gong et al., Pediatrics International (2000) 42, pp. 225-258.
*Effects of Aerosolised Substance P on Lung Resistance in Guinea-Pigs: A Comparison Between Inhibition of Neutral Endopeptidase and Angiotensin-Converting Enzyme*, J. O. Lotvall et al., Br. J. Pharmacol, 1990, 100, pp. 69-72.
Office Action for Korean Patent Application No. 2005-7025128, dated Mar. 15, 2011; 11 pages.
Ortiz, Luis A., et al.; "Enalapril protects mice from pulmonary hypertension by inhibiting TNF-mediated activation of NF-$_K$B and Ap-1"; American Journal of Physiology: Lung Cellular and Molecular Physiology; vol. 282; Jun. 2002; 14 pages.
Newman, Stephen P., "Aerosol Deposition Considerations in Inhalation Therapy", CHEST, 1985; 88, pp. 152s-160s.
Verlag, Editio Cantor, Rote Liste Service GmbH, "Rote Liste 2002, Pres i.v.1,25 mg (27277), Xanef i.v. 1,25 mg (27279)", 2002, *Rote Liste 2002*.
Walmrath, D. et al., *Effects of Inhaled Versus Intravenous Vasodilators in Experimental Pulmonary Hypertension*, EP Respiratory Journal, vol. 19 (1997) 1084-1092.

Welte, M. et al., *PGI$_2$ Aerosol Versus Nitric Oxide for Selective Pulmonary Vasodilation in Hypoxic Pulmonary Vasoconstriction*, Eur Surg Res, vol. 25 (Jun. 4, 1993) 329-340.
Office Action for Japanese Application No. 2014-024822 dated Oct. 6, 2015.
McLaughlin VV J Cardiovasc Pharmacol. Feb. 2003; 41(2):293-9,*Efficacy and safety of treprostinil: an epoprostenol analog for primary pulmonary hypertension*, PMID: 12548091.
Office Action for Russian Patent Application No. 2010152753, dated Dec. 2, 2011; 9 pages.
Boot, H. et al., *Pulmonary Hypertension Complicating Portal Hypertension. A Case Report With Suggestions for a Different Therapeutic Approach*, Eur Heat J., 8(6), Jun. 1987, 656-660.
Aulton, Michael E., *Pharmaceutics the Science of Dosage Form Design*, Churchill Livingstone (2002), 2 pages.
Trenton, D. Nauser et al., *Diagnosis and Treatment of pulmonary hypertension American Family Physician*, May 1, 2011, 63(9):1789-1798.
Office Action for Japanese Application No. 2011-172929; dated May 22, 2013.
Office Action from U.S. Appl. No. 13/020,429 dated Aug. 20, 2015.
Office Action for Korean Application No. 2014-7032775 dated Mar. 5, 2015.
Office Action for Korean Application No. 2012-7015386 dated Jan. 7, 2015.
Office Action from U.S. Appl. No. 13/020,429 dated Mar. 6, 2015.
Office Action from Japanese Patent Application No. 2011-172929 dated Dec. 19, 2014.
Morrell, Nicholas W., et al.; "Angiotensin Converting Enzyme Expression is Increased in Small Pulmonary Arteries of Rats with Hypoxia-induced Pulmonary Hypertension"; *J. Clin. Invest.*; vol. 96, No. 4, 1995; pp. 1823-1833.
Gessler, Tobias, et al.; "Aerosolized Vasodilators in Pulmonary Hypertension"; *J. Aerosol Med.*; 2002; vol. 15, No. 2; pp. 117-122.
Office Action for Canadian Application No. 2,530,632, dated Aug. 12, 2010; 5 pages.
Hache, M., et al; "Inhaled epoprostenol (prostacyclin) and pulmonary hypertension before cardiac surgery"; Journal of Thoracic and Cardiovascular Surgery; 125(1); Mar. 1, 2003; pp. 642-649.
Kemming, G., et al; "Searching for the Ideal Inhaled Vasodilator: From Nitric Oxide to Prostacyclin"; European Surgical Research; 34; 2002; pp. 196-202.
Office Action from Japanese Patent Application No. 2011-172929, dispatched Jan. 12, 2016.
Decision to Decline the Amendment from Japanese Patent Application No. 2011-172929, dispatched Jan. 26, 2016.
Office Action from U.S. Appl. No. 13/020,429, dated Feb. 18, 2016.

\* cited by examiner

INHALABLE FORMULATIONS FOR TREATING PULMONARY HYPERTENSION AND METHODS OF USING SAME

CROSS-REFERENCE TO RELATED APPLICATIONS

The present application is a continuation of PCT/EP2004/006629, filed Jun. 18, 2004, which is a continuation of U.S. application Ser. No. 10/609,233, filed Jun. 27, 2003, which is incorporated herein by reference in its entirety

FIELD OF THE INVENTION

The present invention relates to an inhalable formulation for the treatment of pulmonary hypertension, and methods of treating the same in mammals, including humans. The formulation of the present invention comprises a hypertension reducing agent, wherein the hypertension reducing agent may include an angiotensin-converting enzyme inhibitor ("ACEI"), angiotensin receptor blocker ("ARB"), beta adrenergic blocking agent ("beta-blockers"), calcium-channel blocker or vasodilator, or any combination thereof. Preferably, the formulation of the present invention is suitable for administration via nebulization. The present invention also relates to a prepackaged kit for treating pulmonary hypertension containing the formulation of the present invention.

BACKGROUND OF THE INVENTION

Pulmonary hypertension is a disorder of the lung in which the pressure in the pulmonary artery (the blood vessel that leads from the heart to the lungs) rises above normal levels. If left untreated, pulmonary hypertension may become life threatening. Symptoms of pulmonary hypertension include shortness of breath with minimal exertion, fatigue, chest pain, dizzy spells fainting, and other symptoms. Pulmonary hypertension is frequently misdiagnosed and has often progressed to late stage by the time it is accurately diagnosed. Moreover, pulmonary hypertension has been historically chronic and incurable with a poor survival rate.

When pulmonary hypertension occurs in the absence of a known cause, it is referred to as primary pulmonary hypertension (PPH). There are many unknown causes of PPH.

When the cause of pulmonary hypertension is known, it is called secondary pulmonary hypertension (SPH). Common causes of SPH is the breathing disorders emphysema, bronchitis and chronic obstructive pulmonary disorder, among others. Other less frequent causes are the inflammatory or collagen vascular diseases such as scleroderma, CREST syndrome or systemic lupus erythematosus. Congenital heart diseases that cause shunting of extra blood through the lungs like ventricular and arterial septal defects, chronic pulmonary thromboembolism (old blood clots in the pulmonary artery), HIV infection, liver disease and diet drugs like fenfluramine and dexfenfluramine are also causes of pulmonary hypertension.

Angiotensin-converting enzyme inhibitors (ACEI) are drugs used to treat hypertension (high blood pressure) and congestive heart failure. These drugs are also used to alleviate the strain on hearts damaged from heart attacks. ACEIs block production of an enzyme that helps convert the protein angiotensin I into angiotensin II, a protein that makes blood vessels constrict and promotes retention of fluid in the body, thereby raising blood pressure. ACEIs also make blood vessels relax, which helps lower blood pressure and allows more oxygen-rich blood to reach the heart. Captorpirl (Capoten), Ramipril (Altace, and Enalipril (Vasoted) are commonly used ACE inhibitor.

Angiotensin receptor blockers (ARBs) (also referred to as angiotensin II receptor agonists) such as losartan (COZAAR®) and valsartan (DIOVAN®) reduce hypertension by displacing angiotensin II from receptors on the surface of cells. ARBs are used as alternatives to the less expensive ACEI inhibitors because they have fewer side effects.

Beta-adrenergic blocking agents, or beta-blockers, are used in the treatment of high blood pressure. Beta-blockers are also used to relieve angina (chest pain) and in heart attack patients to help prevent additional heart attacks. Beta-blockers are also used to correct irregular heartbeat, prevent migraine headaches, and treat tremors. Beta-blockers are competitive inhibitors and interfere with the action of stimulating hormones on beta-adrenergic receptors in the nervous system. Beta-blockers can be subdivided into two distinct groups, known as beta-1 and beta-2. Beta-1 blockers mainly affect the heart, and beta-2 blockers mainly affect receptors in bronchial tissue. Most beta-blockers are non-specific, i.e., they have both beta-1 and beta-2 effects.

Calcium-channel blockers are presently used to control hypertension, chest pain and irregular heartbeats. Calcium-channel blockers slow the rate at which calcium passes into the heart muscle and into the vessel walls, thereby relaxing the vessels. The relaxed vessels let blood flow more easily through them, thereby lowering blood pressure.

Vasodilators are medicines that act directly on muscles in blood vessel walls to make blood vessels widen (dilate). Vasodilators are used to treat high blood pressure. By widening the arteries, these drugs allow blood to flow through more easily, reducing blood pressure. Controlling high blood pressure is important because the condition puts a burden on the heart and the arteries, which can lead to permanent damage over time. If untreated, high blood pressure increases the risk of heart attacks, heart failure, stroke, or kidney failure. Examples of vasodilators include prostacyclin and its analogs.

It has been shown that vasodilators such as prostacyclin and prostacyclin analogs as well as calcium channel blockers such as diltiazem (CARDIZEM®) or nifedipine (PROCARDIA®) decrease pulmonary vascular resistance in some patients when administered systemically. For example, it has been found that continuous intravenous infusion of the vasodilator epoprostenol (FLOLAN®), or prostacyclin, improves exercise capacity, quality of life, hemodynamics and long-term survival in patients with primary pulmonary hypertension. Epoprostenol is a potent, short-acting vasodilator and inhibitor of platelet aggregation by vascular endothelium.

Continuous intravenous prostacyclin is far from ideal as a treatment for pulmonary hypertension, however, because the agent is available only in limited supply, it is very costly, and optimal management requires that the intravenous therapy with prostacyclin be started in specialized centers familiar with the technique, equipment, and dose ranging. Moreover, continuous intravenous administration of prostacyclin results in significant side effects in patients, including jaw pain, nausea, and anorexia, plus the inconvenience and potential danger from prolonged cathertization and breakdowns in the delivery system. Further, because the agent is delivered systemically with only a small percentage of the agent actually absorbed by the pulmonary system, it must be administered in high dosages.

Epoprostenol or the prostacyclin analog treprostinil sodium may be administered via injection to treat pulmonary hypertension. Delivery, however, is systemic and not localized to the lung. Thus, the drug must be administered in high doses, with only a small percentage actually reaching the lungs.

It has also been shown that calcium channel blockers may alleviate pulmonary vasoconstriction and prolong life in about 20 percent of patients with PPH. Rich S, Kaufmann E, Levy P S. The effect of high doses of calcium-channel blockers on survival in primary pulmonary hypertension. N Engl J Med 1992; 327:76-81, which is incorporated herein by reference. In patients who show evidence of an acute hemodynamic response, long-term treatment with calcium channel blockers administered orally can produce a sustained hemodynamic response and increase survival. However, oral administration does not produce a localized effect on the lungs and therefore high doses must be administered producing a systemic effect, perhaps unnecessarily. Moreover, oral administration in high dosages over an extended period of time may produce unwanted side-effects in some patients.

There is, therefore, a need for an improved method of treating hypertension.

SUMMARY OF THE INVENTION

The formulations provided herein are used for treating, preventing and/or ameliorating one or more symptoms of a medical condition, disorder or disease. As used herein, treatment means any manner in which one or more of the symptoms of the condition, disorder or disease are ameliorated or otherwise beneficially altered. Treatment also encompasses any pharmaceutical or medicinal use of the formulations herein. As used herein, amelioration of the symptoms of a particular disorder by administration of a particular formulation refers to any lessening, whether permanent or temporary, lasting or transient that can be attributed to or associated with administration of the formulation. As used herein, a "therapeutic effective amount" means a sufficient amount of drug substance to treat, prevent and/or ameliorate one or more symptoms of a medical condition, disorder or disease. It also may include a safe and tolerable amount of drug substance, as based on industry and/or regulatory standards.

In one alternative embodiment, the formulations provided herein are used for treating, preventing and/or ameliorating one or more symptoms of a respiratory disorder in an individual. In another alternative embodiment, the present invention provides a formulation for the treatment, prophylaxis and/or amelioration of one or more symptoms of pulmonary hypertension or other related disorders.

In one preferred embodiment, the present invention provides a formulation for the treatment of pulmonary hypertension in a mammal (e.g., humans), wherein the formulation is suitable for administration via inhalation. Preferably, the formulation of the present invention is suitable for administration via nebulization. The formulations of the present invention comprise a therapeutically effective amount of a hypertension reducing agent. Hypertension reducing agents suitable for use in the present formulations include ACEI, ARBs, beta-blockers, calcium-channel blockers or vasodilators, or any combination thereof. In one alternative embodiment, the formulation of the present invention comprises a combination of two or more hypertension reducing agents.

The formulations of the present inventions may be provided as a solution or as aqueous suspension, so long as the formulation is suitable for inhalation. Preferably, the present formulation is sterile. In another embodiment, the formulation of the present invention is stable. Further, buffering agents may be added to adjust the pH level of the formulation. Moreover, the formulations of the present invention may contain an antimicrobial preservative. Alternatively, the formulations herein may be preservative-free. In one embodiment, the formulations of the present invention are suitable for treating any diagnosis or level of pulmonary hypertension.

The present invention also relates to a method for treating pulmonary hypertension in a mammal, which includes animals or humans. In one embodiment, the method of the present invention comprises the step of administering the formulation of the present invention to a mammal in need thereof. In one embodiment, the method of the present invention further comprises the step of administering another therapy or pharmaceutical agent useful to or related to the treatment of pulmonary hypertension. Such therapies and/or pharmaceutical agents including, for example, anticoagulants and diuretics.

Additionally, the present invention is directed to a kit for treating pulmonary hypertension in a mammal. In one embodiment, the kit of the present invention comprises the formulation of the present invention. In another embodiment, the formulation of the kit is premeasured, premixed and prepackaged. In an alternative embodiment, the kit further comprises instructions for administering the formulation.

Other embodiments, features and advantages of the present invention will be apparent to those of ordinary skill in the art in view of the following detailed description of the invention.

DETAILED DESCRIPTION OF THE INVENTION

As used herein, the terms "angiotensin converting enzyme inhibitor" or "ACEI" means any pharmaceutical agent that inhibits the enzymatic activity of angiotensin converting enzyme. ACEIs suitable for use herein include, but are not limited to, Benazepril, Captopril, Enalapril, Fosinopril, Lisinopril, Moexipril, Perindopril, Quinapril, Ramipril, Trandolapril, and prodrugs, salts and isomers thereof.

As used herein, the terms "angiotensin receptor blocker" or "ARB" or "angiotensin II receptor agonist" means any pharmaceutical agent that selectively blocks the binding of angiotensin II to receptors found in many tissues. ARBs suitable for use herein include, but are not limited to, Candesartan, Eprosartan, Irbesartan, Losartan, Olmesartan, Telmisartan, Valsartan, and prodrugs, salts and isomers thereof.

As used herein, the terms "beta adrenergic blocking agent" or "beta-blocker" means any pharmaceutical agent which blocks beta-adrenergic substances in the body. For example, a beta-blocker may block the beta-adrenergic substance adrenaline (epinephrine), a key agent in the "sympathetic" portion of the autonomic (involuntary) nervous system and activation of heart muscle. Beta-blockers suitable for use herein include, but are not limited to, Acebutolol, Atenolol, Betaxolol, Bisoprolol, Carteolol, Carvedilol, Esmolol, Labetalol, Metoprolol, Nadolol, Oxprenolol, Penbutolol, Pindolol, Propranolol, Sotalol and Timolol and prodrugs, salts and isomers thereof.

As used herein, the term "calcium-channel blocker" means any pharmaceutical agent which slows or blocks the entry of calcium into the muscle cells of the heart and the arteries. Calcium channel blockers suitable for use herein include, but are not limited to, Amlodipine, Bepridil, Diltiazem, Felodipine, Flunarizine, Isradipine, Nicardipine, Nifedipine, Nimodipine, Verapamil and prodrugs, salts and isomers thereof.

As used herein, the term "vasodilator" means any pharmaceutical agent that causes dilation of blood vessels. Vasodilators suitable for use herein include, but are not limited to, Adenine, Arginine, Doxazosin, Hydralazine Hydrochloride, Isosorbide Initrate, Isosorbide Mononitrate Minoxidil, Nicotinates, Nitroglycerin, Phentolamine, Prazosin, Terazosin and prodrugs, salts and isomers thereof. Vasodilators for use herein also include prostaglandins (Eicosanoids), including prostacyclin (Epoprostenol) and prostacyclin analogs, including Iloprost and Treprostinil, and prodrugs, salts and isomers thereof. Also included herein are various prostaglandins, including, but not limited to PGE-1; PGE-2; PGF-2.alpha.; PGA-1; PGB-1; PGD-2; PGE-M; PGF-M; PGH-2; PGI-2; 19-hydroxy-PGA-1; 19-hydroxy-PGB-1; PGA-2; PGB-2; 19-hydroxy-PGA-2; 19-hydroxy-PGB-2; PGB-3; PGF-1.alpha.; 15-methyl-PGF-2.alpha.; 16,16-dimethyl-.DELTA.sup.2-PGE-1 methyl ester; 15-deoxy-16-hydroxy-16-me-thyl-PGE-1 methyl ester; 16,16-dimethyl-PGE-2; 11-deoxy-15-methyl-PGE-1; 16-methyl-18, 18,19,19-tetrahydrocarbacyclin; (16RS)-15-deoxy-16-hydroxy-1-6-methyl-PGE-1 methyl ester; (+)-4,5-didehydro-16-phenoxy-.alpha.-tetranor-PGE-2 methyl ester; 11-deoxy-11a,16,16-trimethyl-PGE-2; (+)-11a,16a,b-dihydroxy-1,9-dioxo-1-(hydroxymethyl)-16-methyl-trans-prostene; 9-chloro-16,16-dimethyl-PGE-2; arboprostil; iloprost; CL 15.347: and semisynthetic or synthetic derivatives of these natural prostaglandins, or any derivative or any prostaglandin analog capable of acting as a vasodilator, and prodrugs, salts and isomers thereof.

As used herein, the term "hypertension reducing pharmaceutical agent" means any ACEI, ARB, beta-blocker, calcium-channel blocker, vasodilator, or any other compound capable of treating pulmonary hypertension through oral inhalation, such as nebulization. It is understood that the above list of hypertension reducing agents include those not currently approved for use in clinical practice in the U.S., and those that will be approved in the future.

As used herein, the term "pulmonary hypertension" means any form, diagnosis, level or stage of pulmonary hypertension, including, but not limited to, primary or secondary pulmonary hypertension, pulmonary arterial hypertension, pulmonary venous hypertension, pulmonary hypertension associated with disorders of the respiratory system or hypothermia, pulmonary hypertension resulting from chronic thrombotic or embolic disease, or pulmonary hypertension resulting from disorders directly affecting the pulmonary vasculature. The term "pulmonary hypertension" also includes other respiratory disorders characterized by acute pulmonary vasoconstriction such as those disorders resulting from pneumonia, traumatic injury, aspiration or inhalation injury, fat embolism in the lung, acidosis inflammation of the lung, adult respiratory distress syndrome, acute pulmonary edema, acute mountain sickness, post-cardiac surgery, acute pulmonary hypertension, persistent pulmonary hypertension of the newborn, perinatal aspiration syndrome, hyaline member disease, acute pulmonary thromboembolism, heparin-protomine reactions, sepsis, status asthamaticus or hypoxia (including iatrogenic hypoxia) and other forms of reversible pulmonary vasoconstriction. Such pulmonary disorders are also characterized by inflammation of the lung including those associated with the migration into the lung of non-resident cell types including the various leucocyte subclasses.

In one alternative embodiment, formulations of the present invention may include pharmaceutically acceptable derivates of a hypertension reducing agent. As used herein, pharmaceutically acceptable derivatives of such compounds include but are not limited to salts, esters, enol ethers, enol esters, acids, bases, solvates, hydrates or prodrugs thereof. Such derivatives may be readily prepared by those of skill in this art using known methods for such derivatization. Such derivatives produced may be administered to animals or humans without substantial toxic effects.

Suitable "pharmaceutically acceptable salts" include conventionally used non-toxic salts, for example a salt with an inorganic base such as an alkali metal salt (such as sodium salt and potassium salt), an alkaline earth metal salt (such as calcium salt and magnesium salt), an ammonium salt; or a salt with an organic base, for example, an amine salt (such as methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino) ethane salt, monomethyl-monoethanolamine salt, procaine salt and caffeine salt), a basic amino acid salt (such as arginine salt and lysine salt), tetraalkyl ammonium salt and the like, or other salt forms that enable the pulmonary hypertension reducing agent to remain soluble in a liquid medium, or to be prepared and/or effectively administered in a liquid medium, preferable an aqueous medium. The above salts may be prepared by a conventional process, for example from the corresponding acid and base or by salt interchange.

For example, one alternative embodiment, the hypertension reducing agent may be employed in a free base form or in a salt form (e.g., as pharmaceutically acceptable salts). Examples of suitable pharmaceutically acceptable salts include inorganic acid addition salts such as hydrochloride, hydrobromide, sulfate, phosphate, and nitrate; organic acid addition salts such as acetate, propionate, succinate, lactate, glycolate, malate, tartrate, citrate, maleate, fumarate, methansulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates.

Examples of the ethers may include, but are not limited to, alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy (lower) alkyl ethers such as hydroxyethyl ether and hydroxyisopropyl ether; lower alkoxy (lower) alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl (lower) alkyl ethers such as benzyl ether, trityl ether and benzhydryl ether, or other ether forms that enable the pulmonary hypertension reducing agent to remain soluble in a liquid medium, or to be prepared and/or effectively administered in a liquid medium, preferably an aqueous medium.

Examples of the esters may include, but are not limited to, aliphatic esters, for example, lower alkyl esters such as methyl ester, ethyl ester, propyl ester, isopropyl ester, butyl ester, isobutyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy (lower) alkyl ester such as hydroxyethyl ester; lower alkoxy (lower) alkyl esters such as methoxymethyl ester and 1-methoxyethyl ester; and optionally substituted aryl esters such as, for example, phenyl ester, tosyl ester, t-butylphenyl ester, salicyl ester, 3,4-di-methoxyphenyl ester and benzamidophenyl ester; and aryl(lower) alkyl ester such as benzyl ester, trityl ester and benzhydryl ester, or other ester forms that enable the pulmonary hypertension reducing agent to remain soluble in a liquid medium, or to be prepared and/or effectively administered in a liquid medium, preferably an aqueous medium.

Also, the hypertension reducing agent for use in the formulations and methods provided herein may contain chiral centers. Such chiral centers may be of either the (R) or (S) configuration, or may be a mixture thereof. Thus, the compounds for use in the formulations provided herein may be enantiomerically pure, or be stereoisomeric or diastereomeric mixtures. It is to be understood that the chiral centers of the compounds provided herein may undergo epimerization in vivo. Thus, one of skill in the art will recognize that administration of a compound in its (R) form is equivalent, for compounds that undergo epimerization in vivo, to administration of the compound in its (S) form.

The present invention provides an inhalable formulation for treating pulmonary hypertension, wherein the formulation comprises a therapeutically effective amount of a hypertension-reducing agent for the treatment of pulmonary hypertension, wherein the hypertension-reducing agent is an ACEI, ARB, beta-blocker, calcium-channel blocker or vasodilator, or any combination thereof.

The present invention is premised, in part, on the known systemic hypertension reducing effects of ACEIs, ARBs, beta-blockers, calcium-channel blockers or vasodilators to treat pulmonary hypertension. It is believed that the formulations of the present invention represent an improvement over conventional means for treating pulmonary hypertension, because the delivery of the hypertension-reducing agent would be localized to the user's pulmonary system, as opposed to systemic delivery. It is believed that localized therapy may increase bioavailability as well as increased efficacy and/or prolonged therapeutic effect. Due to increased bioavailability, the present formulations may contain lower dosages of the hypertension-reducing agents while effectively treating pulmonary hypertension. Additionally, it is believed that localized therapy may result in a decrease in side-effects due to lower dosages and a decrease in patient discomfort and inconvenience due to the less invasive or time-consuming systemic delivery method.

In one embodiment of the present invention, a therapeutically effective amount of a hypertension-reducing agent may include from about 0.001 mg/ml to about 20 mg/ml of an ACEI, ARB, beta-blocker, calcium-channel blocker, vasodilator, or any combination thereof. In an alternative embodiment, a therapeutically effective amount of a hypertension-reducing agent may include from about 0.008 mg/ml to about 15.0 mg/ml. It may also include the following intermediate ranges: about 0.001 mg/ml to about 0.50 mg/ml; about 0.51 mg/ml to about 1.00 mg/ml; about 1.01 mg/ml to about 1.50 mg/ml; about 1.51 mg/ml to about 2.00 mg/ml; about 2.51 mg/ml to about 3.00 mg/ml; about 3.01 mg/ml to about 3.50 mg/ml; about 3.51 mg/ml to about 4.00 mg/ml; about 4.01 mg/ml to about 4.50 mg/ml; about 4.51 mg/ml to about 5.00 mg/ml; about 5.01 mg/ml to about 5.50 mg/ml; about 5.51 mg/ml to about 6.00 mg/ml; about 6.01 mg/ml to about 6.50 mg/ml; about 6.51 mg/ml to about 7.00 mg/ml; about 7.01 mg/ml to about 7.50 mg/ml; about 7.51 mg/ml to about 8.00 mg/ml; about 8.01 mg/ml to about 8.50 mg/ml; about 8.51 mg/ml to about 9.00 mg/ml; about 9.01 mg/ml to about 9.50 mg/ml; about 9.51 mg/ml to about 10.00 mg/ml; about 10.01 mg/ml to about 10.50 mg/ml; about 10.51 mg/ml to about 11.00 mg/ml; about 11.01 mg/ml to about 11.50 mg/ml; about 11.50 mg/ml to about 12.00 mg/ml; about 12.00 mg/ml to about 12.51 mg/ml; about 12.51 mg/ml to about 13.00 mg/ml; about 13.01 mg/ml to about 13.50 mg/ml; about 13.51 mg/ml to about 14.00 mg/ml; about 14.01 mg/ml to about 14.50 mg/ml; about 14.51 mg/ml to about 15.00 mg/ml.

In one alternative embodiment of the present invention, a therapeutically effective amount of a hypertension-reducing agent may include the following intermediate ranges; about 0.001 mg/ml to about 1.0 mg/ml; about 0.005 mg/ml to about 1.0 mg/ml; about 0.01 mg/ml to about 1.0 mg/ml; about 0.05 mg/ml to about 0.1 mg/ml; about 0.05 mg/ml to about 0.5 mg/ml.

In another alternative embodiment of the present invention, a therapeutically effective amount of a hypertension-reducing agent may include from about 0.001 to about 10 mg/ml of a hypertension-reducing pharmaceutical agent, including the following intermediate amounts: about 0.001 mg/ml to about 1.25 mg/ml; about 1.25 mg/ml to about 1.50 mg/ml; about 1.50 mg/ml to about 1.75 mg/ml; about 1.75 mg/ml to about 2.00 mg/ml; about 2.0 mg/ml to about 2.25 mg/ml; about 2.25 mg/ml to about 2.50 mg/ml; about 2.50 mg/ml to about 2.75 mg/ml; about 2.75 mg/ml to about 3.00 mg/ml; about 3.0 mg/ml to about 3.25 mg/ml; about 3.25 mg/ml to about 3.50 mg/ml; about 3.50 mg/ml to about 3.75 mg/ml; about 3.75 mg/ml to about 4.00 mg/ml; about 4.0 mg/ml to about 4.25 mg/ml; about 4.25 mg/ml to about 4.50 mg/ml; about 4.50 mg/ml to about 4.75 mg/ml; about 4.75 mg/ml to about 5.00 mg/ml; about 5.0 mg/ml to about 5.25 mg/ml; about 5.25 mg/ml to about 5.50 mg/ml; about 5.50 mg/ml to about 5.75 mg/ml; about 5.75 mg/ml to about 6.00 mg/ml; about 6.0 mg/ml to about 6.25 mg/ml; about 6.25 mg/ml to about 6.50 mg/ml; about 6.50 mg/ml to about 6.75 mg/ml; about 6.75 mg/ml to about 7.00 mg/ml; about 7.0 mg/ml to about 7.25 mg/ml; about 7.25 mg/ml to about 7.50 mg/ml; about 7.50 mg/ml to about 7.75 mg/ml; about 7.75 mg/ml to about 8.00 mg/ml; about 8.0 mg/ml to about 8.25 mg/ml; about 8.25 mg/ml to about 8.50 mg/ml; about 8.50 mg/ml to about 8.75 mg/ml; about 8.75 mg/ml to about 9.00 mg/ml; about 9.0 mg/ml to about 9.25 mg/ml; about 9.25 mg/ml to about 9.50 mg/ml; about 9.50 mg/ml to about 9.75 mg/ml; about 9.75 mg/ml to about 10.00 mg/ml.

In one embodiment, the formulation of the present invention is an inhalable solution comprising a therapeutically effective amount of a pulmonary hypertension agent. Preferably, the inhalable solution of the present invention is suitable for administration via nebulization. The formulations of the present invention may also be provided as an aqueous suspension. In an embodiment, the formulation of the present invention comprises a therapeutically effective amount of a pulmonary hypertension reducing agent in an aqueous suspension.

The formulations provided herein may comprise any pharmacologically suitable fluid which is physiologically acceptable upon administration, including, but not limited to water, aqueous saline solutions with one or more pharmaceutically acceptable salt(s), alcohols, glycols or any mixture thereof. In an embodiment, the formulation of the present invention comprises water. Water for use in the present formulations should meet or exceed the applicable regulatory requirements for use in inhaled drugs. Specifications established by the United States Pharmacopoeia for "Sterile Water for Injection" or "Sterile Water for Inhalation" are examples of water suitable for use to prepare formulations of the invention.

In one alternate embodiment, the formulation of the present invention may comprise a preservative, suspending agent, wetting agent, tonicity agent and/or diluent. The formulations provided herein may comprise from about 0.01% to about 90%, or about 0.01% to about 50%, or about 0.01% to about 25%, or about 0.01% to about 10%, or about 0.01% to about 5% of one or more pharmacologically suitable suspending fluids which is physiologically acceptable upon administration intranasally. Pharmacologically suitable fluids for use herein include, but are not limited to, polar solvents, including, but not limited to, compounds that contain hydroxyl groups or other polar groups. Solvents include, but are not limited to, water or alcohols, such as ethanol, isopropanol, and glycols including propylene glycol, polyethylene glycol, polypropylene glycol, glycol ether, glycerol and polyoxyethylene alcohols. Polar solvents also include protic solvents, including, but not limited to, water, aqueous saline solutions with one or more pharmaceutically acceptable salt(s), alcohols, glycols or a mixture there of. In one alternative embodiment, the water for use in the present formulations should meet or exceed the applicable regulatory requirements for use in inhaled drugs.

Sterility or adequate antimicrobial preservation may be provided as part of the present formulations. Since certain formulations of the present invention are intended to be administered orally, it is preferred that they be free of pathogenic organisms. A benefit of a sterile liquid suspension is that it reduces the possibility of introducing contaminants into the individual when the suspension formulation is administered intranasally, thereby reducing the chance of an opportunistic infection. Processes which may be considered for achieving sterility may include any appropriate sterilization steps known in the art. In one embodiment, the drug substance (e.g., fluticasone) is produced under sterile conditions, the micronization is performed in a sterile environment, and the mixing and packaging is conducted under sterile conditions. In alternative embodiment, the formulations of the present invention may be sterile filtered and filled in vials, including unit dose vials providing sterile unit dose formulations which are used in a nasal spray device for example. Each unit dose vial may be sterile and is suitably administered without contaminating other vials or the next dose. In one alternative embodiment, one or more ingredients in the present formulation may be sterilized by steam, gamma radiation or prepared using or mixing sterile steroidal powder and other sterile ingredients where appropriate. Also, the formulations may be prepared and handled under sterile conditions, or may be sterilized before or after packaging.

In addition to or in lieu of sterilization, the formulations of the present invention may contain a pharmaceutically acceptable preservative to minimize the possibility of microbial contamination. Additionally, a pharmaceutically-acceptable preservative may be used in the present formulations to increase the stability of the formulations. It should be noted, however, that any preservative must be chosen for inhalation safety, as the treated tissues may be sensitive to irritants. Preservatives suitable for use herein include, but are not limited to, those that protect the solution from contamination with pathogenic particles, including phenylethyl alcohol, benzalkonium chloride or benzoic acid, or benzoates such as sodium benzoate and phenylethyl alcohol. Preferably, the preservative for use in the present formulations is benzalkonium chloride. In certain embodiments, the formulations herein comprise from about 0.001% to about 10.0% w/w of benzalkonium chloride, or from about 0.01% v/w phenylethyl alcohol. Preserving agents may also be present in an amount from about 0.001% to about 1%, preferably about 0.002% to about 0.02%, more preferably 0.02% w/w.

The formulations provided herein may also comprise from about 0.001% to about 90%, or about 0.001% to about 50%, or about 0.001% to about 25%, or about 0.001% to about 10%, or about 0.001% to about 1% of one or more emulsifying agent, wetting agent, or suspending agent. Such agents for use herein include, but are not limited to, polyoxyethylene sorbitan fatty esters or polysorbates, including, but not limited to, polyethylene sorbitan monooleate (Polysorbate 80), polysorbate 20 (polyoxyethylene (20) sorbitan monolaurate), polysorbate 65 (polyoxyethylene (20) sorbitan tristearate), polyoxyethylene (20) sorbitan mono-oleate, polyoxyethylene (20) sorbitan monopalmitate, polyoxyethylene (20) sorbitan monostearate; lecithins; alginic acid; sodium alginate; potassium alginate; ammonium alginate; calcium alginate; propane-1,2-diol alginate; agar; carrageenan; locust bean gum; guar gum; tragacanth; acacia; xanthan gum; karaya gum; pectin; amidated pectin; ammonium phosphatides; microcrystalline cellulose; methylcellulose; hydroxypropylcellulose; hydroxypropylmethylcellulose; ethylmethylcellulose; carboxymethylcellulose; sodium, potassium and calcium salts of fatty acids; mono- and di-glycerides of fatty acids; acetic acid esters of mono- and di-glycerides of fatty acids; lactic acid esters of mono- and di-glycerides of fatty acids; citric acid esters of mono- and di-glycerides of fatty acids; tartaric acid esters of mono- and di-glycerides of fatty acids; mono- and diacetyltartaric acid esters of mono- and di-glycerides of fatty acids; mixed acetic and tartaric acid esters of mono- and di-glycerides of fatty acids; sucrose esters of fatty acids; sucroglycerides; polyglycerol esters of fatty acids; polyglycerol esters of polycondensed fatty acids of castor oil; propane-1,2-diol esters of fatty acids; sodium stearoyl-21 actylate; calcium stearoyl-2-lactylate; stearoyl tartrate; sorbitan monostearate; sorbitan tristearate; sorbitan monolaurate; sorbitan monooleate; sorbitan monopalmitate; extract of quillaia; polyglycerol esters of dimerised fatty acids of soya bean oil; oxidatively polymerised soya bean oil; and pectin extract.

The present formulations may further comprise from about 0.001% to about 90%, or about 0.001% to about 50%, or about 0.001% to about 25%, or about 0.001% to about 10%, or about 0.001% to about 1% of one or more excipients and additives which are pharmacologically suitable. Excipients and additives generally have no pharmacological activity, or at least no undesirable pharmacological activity. The concentration of these may vary with the selected agent, although the presence or absence of these agents, or their concentration is not an essential feature of the invention. The excipients and additives may include, but are not limited to, surfactants, moisturizers, stabilizers, complexing agents, antioxidants, or other additives known in the art. Complexing agents include, but are not limited to, ethylenediaminetetraacetic acid (EDTA) or a salt thereof, such as the disodium salt, citric acid, nitrilotriacetic acid and the salts thereof. In another embodiment, particularly in the suspension formulations provided herein, the complexing agent is sodium edetate. In one embodiment, the compositions contain sodium edetate at a concentration of about 0.05 mg/ml to about 0.5 mg/ml, or about 0.1 mg/ml to about 0.2 mg/ml. Also, for example, the formulations of the present invention may comprise from about 0.001% to about 5% by weight of a humectant to inhibit drying of the mucous membrane and to prevent irritation. Any of a variety of pharmaceutically-acceptable humectants can be employed, including sorbitol, propylene glycol, polyethylene glycol, glycerol or mixtures thereof, for example.

The formulations provided herein also may comprise about 0.001% to about 90%, or about 0.001% to about 50%, or about 0.001% to about 25%, or about 0.001% to about 10%, or about 0.001% to about 10% of one or more solvents or co-solvents to increase the solubility of any of the components of the present formulation. Solvents or co-solvents for use herein include, but are not limited to, hydroxylated solvents or other pharmaceutically-acceptable polar solvents, such as alcohols including isopropyl alcohol, glycols such as propylene glycol, polyethylene glycol, polypropylene glycol, glycol ether, glycerol, and polyoxyethylene alcohols. In another embodiment, the formulations of the present invention may comprise one or more conventional diluents known in the art. The preferred diluent is purified water.

Tonicity agents (or osmotic adjusting agents) may be added to adjust the isotonicity of the present formulations. Such agents may include, but are not limited to sodium chloride, potassium chloride, zinc chloride, calcium chloride or mixtures thereof. Other osmotic adjusting agents may also include, but are not limited to, mannitol, glycerol, and dextrose or mixtures thereof. In an alternative embodiment, the present formulation may comprise about 0.01% to about 10% w/w, or 1% to about 6% w/w. In one alternative embodiment, the formulations of the present invention are isotonic.

In certain embodiments herein, the formulations of the present invention have a pH of about 2.0 to about 8.0. Preferably, the pH of the present formulations is from about 3.0 to about 6.0, preferably the pH is form about 3.0 to about 4.0. Optionally, the formulations of the present invention contain a pH buffer to maintain the formulation to a desired pH. Buffers suitable for use herein include, but are not limited to, citric acid/phosphate, sodium hydroxide, sodium citrate, acetate, barbital, borate, Britton-Robinson, cacodylate, citrate, collidine, formate, maleate, Mclivaine, phosphate, Prideaux-Ward, succinate, citrate-phosphate-borate (Teorell-Stanhagen), veronal acetate, MES (2-(N-morpholino)ethanesulfonic acid), BIS-TRIS (bis(2-hydroxyethyl)imino-tris(hydroxymethyl)methane), ADA (N-(2-acetamido)-2-iminodiacetic acid), ACES (N-(carbamoylmethyl)-2-aminoethanesulfonaic acid), PIPES (piperazine-N,N'-bis(2-ethanesulfonic acid)), MOPSO (3-(N-morpholino)-2hydroxypropanesulfonic acid), BIS-TRIS PROPANE (1,3-bis(tris(hydroxy-methyl)methylamino)propane), BES (N,N-bis(2-hydroxyethyl)-2-aminoethanesulfonaic acid), MOPS (3-(N-morpholino)propanesulfonic acid), TES (N-tris(hydroxymethyl)methyl-2-aminoethanesulfonic.acid), HEPES (N-(2hydroxyethyl)piperazine-N'-(2-etha-nesulfonicacid), DIPSO (3-(N,N-bis(2hydroxyethyl)amino)-2-hydroxypropanesu-lfonicacid), MOBS (4-(N-morpholino)butanesulfonic acid), TAPSO (3-(N-tris(hydroxymethyl)methylamino)-2-hydroxypropanesulfonic acid), TRIZMAO (tris(hydroxymethylaminomethane), HEPPSO (N-(2-hydroxyethyl)piper-azine-N'-(2-hydroxypropanesulfonic acid), POPSO (piperazine-N,N'-bis(2-hydroxypropanesulfonic acid)), TEA (triethanolamine), EPPS (N-(2-hydroxyethyl)-piperazine-N'-(3-propanesulfonic acid), TRICINE (N-tris(hydroxymethyl)met-hylglycine), GLY-GLY (glycylglycine), BICINE (N,N-bis(2hydroxyethyl)glycin-e), HEPBS(N-(2-hydroxyethyl)piperazine-N'-(4butanesulfonic acid)), TAPS(N-tris(hydroxymethyl)methyl-3-aminopropanesulfonic acid), AMPD (2-amino-2-methyl-1,3-propanediol), and/or any other buffers known to those of skill in the art.

In one alternative embodiment, the formulations of the present invention are stable. As used herein, the stability of formulations provided herein refers to the length of time at a given temperature that greater than 80%, 85%, 90% or 95% of the initial amount of drug substance, e.g., fluticasone, is present in the formulation. For example, the formulations provided herein may be stored between about 15° C. and about 30° C., and remain stable for at least 1, 2, 12, 18, 24 or 36 months. Also, the formulations may be suitable for administration to a subject in need thereof after storage for more than 1, 2, 12, 18, 24 or 36 months at 25°. Also, in another alternative embodiment, using Arrhenius Kinetics, more than 80%, or more than 85%, or more than 90%, or more than 95% of the initial amount of drug substance (e.g., fluticasone) remains after storage of the formulations for more than 1, 2, 12, 18, 24 or 36 months between about 15° C. and about 30° C.

As used herein, the statement that a composition is stable during "long term storage" means that the composition is suitable for administration to a subject in need thereof when it has an estimated shelf-life of greater than 1, 2 or 3 months usage time at 25° C. and greater than or equal to 1, 2 or 3 years storage time at 5° C. In certain embodiments herein, using Arrhenius kinetics, >80% or >85% or >90% or >95% estimated bronchodilating agent remains after such storage.

The formulations of the present invention may be administered in a variety of ways, preferably by inhalation. For example, the present formulations may be administered to an individual in need thereof by way of an inhaler, e.g., metered dose inhaler or a dry powder inhaler, an insufflator, a nebulizer or any other conventionally known method of administering inhalable medicaments. Preferably, the formulation of the present invention is administered by nebulization. In one alternative embodiment, the formulations of the present invention may be administered by way of a pressurized aerosol comprising, separately, a hypertension-reducing agent, or salt or an ester thereof with at least a suitable propellant or with a surfactant or a mixture of surfactants. Any conventionally known propellant may be used.

In certain embodiments, the compositions are administered via nebulization. Administration of a nebulized aerosol is preferred over the use of dry powders for inhalation in certain subject populations, including pediatric and geriatric groups.

Also provided herein are combinations containing a composition provided herein and a nebulizer. The combinations can be packaged as kits, which optionally contain other components, including instructions for use of the nebulizer. Any nebulizer is contemplated for use in the kits and methods provided herein. In particular, the nebulizers for use herein nebulize liquid formulations, including the compositions provided herein, containing no propellant. The nebulizer may produce the nebulized mist by any method known to those of skill in the art, including, but not limited to, compressed air, ultrasonic waves, or vibration. The nebulizer may further have an internal baffle. The internal baffle, together with the housing of the nebulizer, selectively removes large droplets from the mist by impaction and allows the droplets to return to the reservoir. The fine aerosol droplets thus produced are entrained into the lung by the inhaling air/oxygen.

As used herein, a nebulized solution refers to a solution that is dispersed in air to form an aerosol. Thus, a nebulized solution is a particular form of an aerosol. As used herein, a nebulizer is an instrument that is capable of generating very fine liquid droplet for inhalation into the lung. Within this instrument, the nebulizing liquid or solution is atomized into a mist of droplets with a broad size distribution by methods known to those of skill in the art, including, but not limited to, compressed air, ultrasonic waves, or a vibrating orifice. Nebulizers may further contain, e.g., a baffle which, along with the housing of the instrument, selectively removes large droplets from the mist by impaction. Thus, the mist inhaled into the lung contains fine aerosol droplets.

In one alternative embodiment, the compositions provided herein are intended for administration to subject in need of such treatment via nebulization. Nebulizers that nebulize liquid formulations containing no propellant are suitable for use with the compositions provided herein. Nebulizers are available from, e.g., Pari GmbH (Starnberg, Germany), DeVilbiss Healthcare (Heston, Middlesex, UK), Healthdyne, Vital Signs, Baxter, Allied Health Care, Invacare, Hudson, Omron, Bremed, AirSep, Luminscope, Medisana, Siemens, Aerogen, Mountain Medical, Aerosol Medical Ltd. (Colchester, Essex, UK), AFP Medical (Rugby, Warwickshire, UK), Bard Ltd. (Sunderland, UK), Carri-Med Ltd. (Dorking, UK), Plaem Nuiva (Brescia, Italy), Henleys Medical Supplies (London, UK), Intersurgical (Berkshire, UK), Lifecare Hospital Supplies (Leies, UK), Medic-Aid Ltd. (West Sussex, UK), Medix Ltd. (Essex, UK), Sinclair Medical Ltd. (Surrey, UK), and many others.

Nebulizers for use herein include, but are not limited to, jet nebulizers (optionally sold with compressors), ultrasonic nebulizers, and others. Exemplary jet nebulizers for use herein include Pari LC plus/ProNeb, Pari LC plus/ProNeb Turbo, Pari LC plus/Dura Neb 1000 & 2000, Pari LC plus/Walkhaler, Pari LC plus/Pari Master, Pari LC star, Omron CompAir XL Portable Nebulizer System (NE-C18 and JetAir Disposable nebulizer), Omron CompAir Elite Compressor Nebulizer System (NE-C21 and Elite Air Reusable Nebilizer), Pari LC Plus or Pari LC Star nebulizer with Proneb Ultra compressor, Pulmo-aide, Pulmo-aide LT, Pulmo-aide traveler, Invacare Passport, Inspiration Healthdyne 626, Pulmo-Neb Traverier, DeVilbiss 646, Whisper Jet, Acorn 11, Misty-Neb, Allied aerosol, Schuco Home Care, Lexan Plasic Pocet Neb, SideStream Hand Held Neb, Mobil Mist, Up-Draft, Up-Draft 11, T Up-Draft, ISO-NEB, AVA-NEB, Micro Mist, and PulmoMate. Exemplary ultrasonic nebulizers for use herein include MicroAir, UltraAir, Siemens Ultra Nebulizer 145, CompAir, Pulmosonic, Scout, 5003 Ultrasonic Neb, 5110 Ultrasonic Neb, 5004 Desk Ultrasonic Nebulizer, Mystique Ultrasonic, Luminscope's Ultrasonic Nebulizer, Medisana Ultrasonic Nebulizer, Microstat Ultrasonic Nebulizer, and MABISMist Hand Held Ultrasonic Nebulizer. Other nebulizers for use herein include 5000 Electromagnetic Neb, 5001 Electromagnetic Neb 5002 Rotary Piston Neb, Lumineb I Piston Nebulizer 5500, Aeroneb' Portable Nebulizer System, Aerodose" Inhaler, and AeroEclipse Breath Actuated Nebulizer.

Pharmaceutical compositions containing a pulmonary hypertension reducing agent for administration via nebulization are provided. The compositions may be sterile filtered and filled in vials, including unit dose vials providing sterile unit dose formulations which are used in a nebulizer and suitably nebulized. Each unit dose vial may be sterile and suitably nebulized without contaminating other vials or the next dose.

The unit dose vials may be formed in a form-fill-seal machine or by any other suitable method known to those of skill in the art. The vials may be made of plastic materials that are suitably used in these processes. For example, plastic materials for preparing the unit dose vials include, but are not limited to, low density polyethylene, high density polyethylene, polypropylene and polyesters. In one embodiment, the plastic material is low density polyethylene.

In another alternative embodiment, the system of the present invention comprises one or more dispensing containers prefilled with about 0.1 to about 5.0 ml, or about 0.5 ml to about 5.0 ml, or about 1.0 ml to about 5.0 ml; or about 0.1 ml to about 3.0 ml, or about 0.1 ml to about 2.0 ml, or about 0.5 ml to about 2.0 ml, or about 1 ml, or about 1.5 ml, or about 2.0 ml, or about 2.5 ml, or about 3.0 ml, or about 3.5 ml, or about 4.0 ml, or about 4.5 ml, or about 5.0 ml, or about 0.1 ml to about 2.25 ml, or about 1.0 ml to about 2.0 ml, or about 2.0 ml to about 2.4 ml of a premixed, premeasured, aqueous inhalation solution comprising a single unit dose of a therapeutically effective amount of one or more pulmonary hypertension reducing agents.

Drugs administered by nebulization could play a major role in the treatment of pulmonary hypertension. However, a possible drawback of nebulization therapy is the number of times it must be performed each day, and the amount of time each treatment takes. For example, an individual may be required to receive 4 doses of inhalation solution per day by nebulization. In some instances, each nebulizer treatment takes about 15 minutes, or more to deliver a 2.5 ml fill volume of a bronchodilator, though the amount of time may vary depending on the model of the nebulizer used. The time requirements for nebulization therapy can be burdensome, and cause individuals to skip required dosages during the day. The impact of not following the prescribed dosage regimen could compromise the individual's condition.

In one alternative embodiment, the volume of the one or more pulmonary hypertension reducing agents inhalation solutions of the present invention is about 0.1 ml to about 2.25 ml, or about 0.1 ml to about 2 ml, or about 1 ml to about 2 ml, or about 1.5 ml to about 2 ml, preferably about 1 ml, about 1.5 ml, about 2.0 ml, or about 2.25 ml while no clinical trials or other experiments were carried out on these fill volumes, it is believed that such volumes are more beneficial over conventional nebulizer fill volumes solutions (e.g. 2.5 ml or 3.0 ml fill volume) because they will enable the individual to receive more medication (e.g., one or more pulmonary hypertension reducing agents) in less time during each nebulization treatment. Also, it is believed that the fill volumes of the present invention will minimize common handling complications with nebulizer therapy, and it may extend the life of the nebulizer.

In one alternative embodiment, the above fill volumes of the present invention may reduce the time of each nebulization treatment by at least 20%, 30%, 40%, 50%, 60%, 70% or 80% or more over conventional nebulizer treatments (e.g. 2.5 ml or 3 ml fill volume). In another alternative embodiment, the fill volumes of the present invention may reduce each nebulization treatment to about 12, 10, 9, 8, 6, 5, 4, 3 minutes, or less over conventional nebulizer treatments (e.g. 2.5 ml or 3.0 ml fill volume). Reducing the amount of time to complete the treatment means individuals will be more likely to comply with the prescribed dosing regimen and achieve optimal benefit from the medication prescribed.

Another possible drawback of conventional nebulizer treatments is the loss of medication during administration. Conventional nebulizer solutions comprise about 2.5 ml fill volume of inhalation solution, or more. For example, when nebulizing an inhalation solution comprising 2.5 ml or more, about 0.7 ml of the solution remains in the nebulizer system after treatment, though the amount may vary depending on the model of the nebulizer used. In these instances, the individual is not receiving the prescribed dosage or optimum dosage of inhalation medication. For example, in one day, due to the residual medication remaining in the nebulizer system after each treatment, an individual fails to receive approximately 2.1 ml, or more of the prescribed daily amount of medication.

It is believed that the fill volumes of the one or more pulmonary hypertension reducing agents inhalation solutions of the present invention will result in lesser amounts of solution remaining in the nebulizer system after treatment, when compared to conventional inhalation solutions (e.g. 2.5 ml or 3 ml fill volume). Less solution remaining in the nebulizer system means more medication (e.g., one or more pulmonary hypertension reducing agents) administered to the individual during each treatment. In one alternative embodiment, the amount of solution remaining in the nebulizer system after each treatment may be less than 0.50 ml, or less than 0.30 ml, or less than 0.20 ml or less than 0.10 ml or less than 0.05 ml of the one or more pulmonary hypertension reducing agents inhalation solutions of the present invention, e.g. an inhalation solution comprising 2.5 mg albuterol and 0.5 mg ipratropium bromide.

Important factors to effective nebulizer treatment is deep inspiration to ensure deep penetration of the medication into the lungs, and steady breath-holding to ensure good retention of the medication in the lungs. It is believed that administering about 0.1 ml to about 2.0 ml fill volume of an inhalation solution into a nebulizer, for example, will optimize the therapeutic effect of the individual's deep inspiration efforts during treatment, and will optimize the therapeutic effect of the individual's breath-holding efforts as well. This is due to the shorter treatment time and increased concentration of the one or more pulmonary hypertension reducing agents in the solution.

Accordingly, in one alternative embodiment, the present invention is a method of facilitating patient care, reducing medication error, reducing nebulizer treatment time, improving the efficiency and efficacy of nebulizing therapy or enhancing therapeutic compliance of an individual suffering from pulmonary hypertension. In one alternative embodiment, such method may comprise the step of placing about 0.1 ml to about 2.0 ml of the inhalation solutions of the present invention into a chamber of a nebulizer. The nebulizer having a mouthpiece or facemask associated with the chamber of the nebulizer. The mouthpiece or facemask is positioned in close proximity to the individual's mouth or face. The inhalation solution may be passed in a mist form from the nebulizer chamber through the mouthpiece or facemask to the individual while the individual breathes into the mouthpiece or facemask. The individual continues breathing into the mouthpiece or facemask until the nebulization treatment is finished. This may take about 12, 11, 10, 9, 8, 7, 6, 5, 4 or 3 minutes. In an alternative embodiment, the nebulization treatment is finished when at least substantially all the mist is removed from the nebulizer chamber. This may take about 12, 11, 10, 9, 8, 7, 6, 5, 4, or 3 minutes. In one alternative embodiment of the present invention, the dose of the inhalation solution in each of the one or more containers may be administered 1, 2, 3, 4, 5, 6, 7, or 8 times per day by nebulization.

In another alternative embodiment, the system/kit of the present invention may further comprise a label which indicates that the inhalation solution can be used to relieve bronchospasm associated with chronic obstructive pulmonary disease. In one alternative embodiment, the label may comprise indicia comprising efficacy, dosage, administration, contraindication and adverse reaction data pertaining to the inhalation solution in each of the one or more containers. The contraindication data may comprise data indicating that the inhalation solution in each of the one or more containers is contraindicated for humans with hypersensitivity to any of the ingredients contained in the inhalation solution.

The dosage and administration data may also comprise data indicating that the recommended dose of the inhalation solution in each of the one or more containers may be administered 1, 2, 3, 4, 5, 6, 7 or 8 times per day by nebulization.

In an alternative embodiment, the present invention also comprises a device for use in the relief of symptoms associated with pulmonary hypertension, including bronchospasm. Such device may take the form of a label, written instructions or any other form incorporating indicia thereon. The device may comprise indicia which indicates that a patient suffering from symptoms associated with pulmonary hypertension can be treated with at least one prepackaged, sterile, premixed, premeasured and/or BAC-free inhalation solution comprising a unit dose of a therapeutically effective amount of one or more pulmonary hypertension reducing agents in a single vial. The inhalation solution being suitable for nebulization in a nebulizer. The device may also comprise indicia which provides instructions for utilizing the inhalation solution to treat said symptoms in patients.

The inhalation formulations of the present invention may be used to treat "pulmonary hypertension" (as that term is defined herein) including but not limited to primary pulmonary hypertension, secondary hypertension, and classes I-IV as shown in Table 1, among others. For example, the formulations of the present invention may be used to treat or ameliorate one or more of the following symptoms of pulmonary hypertension associated with disorders of the respiratory system and/or hypoxemia: chronic obstructive pulmonary disease, interstitial lung disease, sleep-disordered breathing; alveolar hypoventilation disorders; chronic exposure to high altitudes; neonatal lung disease; and alveolar-capillary dysplasia. The information in Table I is presented for illustrative purposes only. It is not intended to limit the scope of the invention.

TABLE 1

| Class Description |
|---|

| Class | Description |
|---|---|
| I | Patients with pulmonary hypertension but without resulting limitation of physical activity. Ordinary physical activity does not cause undue dyspnea or fatigue, chest pain or near syncope. |

TABLE 1-continued

| Class | Description |
|---|---|
| II | Patients with pulmonary hypertension resulting in slight limitation of physical activity. These patients are comfortable at rest, but ordinary physical activity causes undue dyspnea or fatigue, chest pain or near syncope. |
| III | Patients with pulmonary hypertension resulting in marked limitation of physical activity. These patients are comfortable at rest, but less than ordinary physical activity causes undue dyspnea or fatigue, chest pain or near syncope. |
| IV | Patients with pulmonary hypertension resulting in inability to perform any physical activity without symptoms. These patients manifest signs of right heart failure. Dyspnea and/or fatigue may be present at rest, and discomfort is increased by any physical activity. |

The formulations of the present invention may comprise one or more pulmonary hypertension reducing agents. In one embodiment, the formulation of the present invention comprises one of an ACEI, ARB, beta-blocker, calcium-channel blocker or vasodilator, or any combination thereof. Such combination may explicitly exclude any one of the pulmonary reducing agents herein. In an alternative embodiment, the formulation of the present invention comprises an ACEI in combination with an ARB, beta-blocker, calcium-channel blocker or vasodilator. In another embodiment, the formulation of the present invention comprises an ARB in combination with a beta-blocker, calcium-channel blocker or vasodilator. In yet another embodiment, the formulation of the present invention comprises a beta-blocker in combination with a calcium-channel blocker or vasodilator. In still another embodiment, the formulation of the present invention comprises a calcium-channel blocker and a vasodilator. In an alternative embodiment herein, the present invention comprises any combination of at least three ACEIs, ARBs, beta-blockers, calcium-channel blockers or vasodilators.

Additionally, the formulations of the present invention may be administered together with one or more other drugs or therapies. For example, the present formulations may be administered with an anticoagulant such as warfarin (Coumadin), which is recommended to prevent thrombosis and has been shown to prolong life in patients with primary pulmonary hypertension. Patients with pulmonary hypertension are prone to thromboembolism because of sluggish pulmonary blood flow, dilated right heart chambers, venous insufficiency and relative physical inactivity.

Additionally, the formulations of the present invention may be administered in conjunction or in combination with inotropic agents such as digoxin (Lanoxin), which has been shown to produce favorable acute hemodynamic effects in patients with right ventricular failure and primary pulmonary hypertension. Short-term parenterally administered inotropic drugs may also be administered with the formulations of the present invention. Moreover, because hypoxia is a potent pulmonary vasoconstrictor, the formulations of the present invention may be administered in combination with low-flow supplemental oxygen therapy, which is known to prolong survival in hypoxemic patients.

Additionally, the formulations of the present invention may be administered in combination with a low-salt diet and/or diuretics, which are useful in reducing volume overload in patients with pulmonary hypertension and right ventricular failure. However, excessive diuresis and further reduction of cardiac output should be avoided.

The present invention is also directed to a method of treating pulmonary hypertension in a mammal including animals and humans. In one embodiment, a therapeutically effective amount of a hypertension-reducing pharmaceutical agent is administered to a mammal in need thereof. In an alternative embodiment, the formulation of the present invention is premeasured, premixed and prepackaged. In one embodiment, the formulation of the method of the present invention comprises from about 0.01 mg/ml to about 20 mg/ml of at least one of an ACEI, ARB, beta-blocker, calcium-channel blocker or vasodilator, or any combination thereof. In an alternative embodiment, the formulation is sterile and/or stable. In another embodiment, the formulation is preservative-free.

In another alternative embodiment, the method of the present invention comprises the step of administering to a mammal in need thereof an inhalation solution comprising a therapeutically effective amount of a hypertension-reducing pharmaceutical agent, wherein the inhalation solution is administered via nebulizer, such nebulizer including, but not limited to, a jet nebulizer, ultrasonic nebulizer and breath-actuated nebulizer. Preferably, the nebulizer is a jet nebulizer connected to an air compressor with adequate air flow. The nebulizer being equipped with a mouthpiece or suitable face mask.

The present invention is also directed to a system and/or kit for treating pulmonary hypertension in a mammal. In an embodiment, the kit of the present invention comprises a formulation comprising a therapeutically effective amount of a pulmonary hypertension reducing agent. In an alternative embodiment, the formulation is in premeasured, premixed and/or prepackaged. Preferably, the inhalation solution is sterile.

The system and/or kit of the present invention may also include instructions designed to facilitate user compliance. Instructions, as used herein, refers to any label, insert, etc., and may be positioned on one or more surfaces of the packaging material, or the instructions may be provided on a separate sheet, or any combination thereof. For example, in an embodiment, a system and/or kit of the present invention comprises instructions for administering the formulations of the present invention. In one embodiment, the instructions indicate that the formulation of the present invention is suitable for the treatment of pulmonary hypertension. Such instructions may also include instructions on dosage, as well as instructions for administration via nebulizer.

Non-adherence to pulmonary hypertension medication therapy and medication error could be considerable problems. These problems can be significantly reduced by providing pulmonary hypertension patients a prepackaged, premixed, premeasured amount an inhalable formulation comprising one or more pulmonary hypertension reducing agents. Providing these compounds in this fashion makes pulmonary hypertension therapy simple because it increases convenience and eliminates confusion in preparing appropriate dosages.

In one alternative embodiment, the present invention may overcome the aforementioned problems by providing therapeutically effective amounts one or more hypertension reducing agents in prepackaged, premixed, premeasured and/or unit dose amounts. In one alternative embodiment, the present invention comprises one or more prefilled containers. The one or more containers each comprising a single unit dose of an aqueous solution comprising a therapeutically effective amount of one or more pulmonary hypertension reducing agents. Providing the inhalation solution in such a manner eliminates the need to dilute or mix such medications to obtain proper dosages for treatment. Also, no special pharmacy compounding is required, thereby reducing the chance of medication errors. Further, there is a lower risk of cross-contamination, and less waste of medication when providing an inhalation solution in a premixed, ready to use form.

Other features of the present invention include improved user compliance and quality of life as compared to conventional treatments for pulmonary hypertension. While the level of compliance of any pulmonary hypertension treatment depends in part on the motivation of the user and the skill of the individual dispensing the treatment, compliance nevertheless may be improved by controlling factors such as the ease with which the treatment may be administered, as well as the desirability of receiving the treatment.

The present invention provides a convenient, fast and reliable treatment for pulmonary hypertension and clearly represents an improvement over traditional pulmonary hypertension treatments. Also, the present invention is designed to facilitate user compliance by providing one or more dispensing containers comprising a premixed, premeasured inhalation solution comprising a single unit dose of a therapeutically effective amount of one or more pulmonary hypertension reducing agents for the treatment of pulmonary hypertension. Such containers may be utilized in a method of treating pulmonary hypertension or the containers may be incorporated in a system and/or kit for treating the same.

In another embodiment, the present invention provides a system and/or kit for organizing and storing one or more prefilled dispensing containers, each container comprising a premixed, premeasured inhalation solution. The inhalation solution comprising a single unit dose of a therapeutically effective amount one or more pulmonary hypertension reducing agents. Such system and/or kit may provide such containers in prepackaged form. The one or more containers may be comprised of plastic including, but not limited to, a semi-permeable plastic such as LDPE. The container may also comprise a Twist-Flex™ top, such top comprising an easy-to-grip tab-like handle such that the container may be opened, for example, by twisting off the tab by hand. The Twist-Flex™ top is advantageous in that it allows for easy dispensing of the solution, prevents spillage and eliminates the need to open the container by cutting or tearing off the top, or the like, thereby reducing cross-contamination. In one alternative embodiment, the design of the container substantially conforms to those designs illustrated in U.S. Pat. Des. Nos. 317,715; 296,869; 289,609; or 275,732, which are incorporated herein by reference. One or more of the semi-permeable single unit dose containers may be prepackaged in an aluminum foil pouch, such that the foil provides a protective barrier against environmental contaminants and light. Such a barrier improves the shelf-life and stability of the inhalation solution.

In another alternative embodiment, the present invention comprises a prepackaged inhalation system and/or kit suitable for patients suffering from pulmonary hypertension. Such prepackaged system and/or kit comprising: (a) one or more single unit dosages of a therapeutically effective amount of one or more pulmonary hypertension reducing agents; (b) administration instructions for the use of said unit dose as a treatment for pulmonary hypertension; and (c) a dispensing container prefilled with the one or more unit doses of one or more pulmonary hypertension reducing agents.

The formulations of the present invention may be manufactured in any conventional manner by thoroughly mixing the ingredients described herein at ambient or elevated temperatures in order to achieve solubility of ingredients where appropriate.

Articles of manufacture, containing packaging material, a formulation provided herein, may be useful for treatment, prevention or amelioration of one or more symptoms of diseases or disorders associated with pulmonary hypertension. such articles of manufacture may also comprise a label that indicates that the composition is used for treatment, prevention or amelioration of one or more symptoms of diseases or disorders associated with pulmonary hypertension.

In one alternative embodiments, the articles of manufacture provided herein contain packaging materials. Packaging materials for use in packaging pharmaceutical products are well known to those of skill in the art. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

EXAMPLES

Examples 1-4 herein are prophetic examples provided to illustrate, but not to limit, the formulations and methods of the present invention. They are presented with the understanding that changes can be and may need to be made to a specific composition in order to obtain or optimize the formulation. Such modifications to the following prophetic examples, if needed, are normal and understandable to those of ordinary skill in the art, and shall not be used to limit the invention.

It is believed that prophetic examples 1-4 would be suitable for administration via nebulization to an individual suffering from pulmonary hypertension. The formulations may be sterile. The objective of these formulations is to provide localized delivery of a pulmonary hypertension reducing agent to a mammal (e.g. humans) in need thereof.

Example 1

| | |
|---|---|
| Enalaprilat (s-1-[N-(1-carboxy-3-phenylpropyl)-L-alanyl]-L-praline dehydrate | 0.2-10.0 mg/ml |
| Sodium Chloride | 2.0-10.0 mg/ml |
| Sodium Hydroxide | q.s. |
| Water | q.s. |

Example 1 is a prophetic example of a formulation comprising the ACEI enalapril. Sodium chloride may be added to the solution to adjust tonicity, and sodium hydroxide may be added to adjust the pH of the solution. The solution of Example 1 may be made by methods known to those of ordinary skill in the art.

Example 2

| | |
|---|---|
| Atenolol (Benzeneacetamide, 4-[2-hydroxy-3-(1-methylethyl)amino propoxy] | 1.0-10.0 mg/ml |
| Sodium Chloride | 2.0-10.0 mg/ml |
| Sodium Citrate | q.s. |
| Citric Acid | q.s. |
| Water | q.s. |

Example 2 is a prophetic example of a formulation comprising the beta-blocker atenolol. Sodium chloride may be added to the solution to adjust tonicity, and sodium hydroxide and citric acid are added to adjust the pH of the solution. The solution of Example 2 may be made by methods known to those of ordinary skill in the art.

Example 3

| | |
|---|---|
| Epoprostenol | 0.1-3.0 mg/ml |
| Span 85 | 0.2-2.0 mg/ml |
| Water | q.s. |

Example 3 is a prophetic example of a formulation comprising the vasodilator epoprostenol in suspension form. Span 85 may be added as an emulsifier. The suspension of Example 3 may be made by methods known to those of ordinary skill in the art.

Example 4

| | |
|---|---|
| Treprostinil sodium | 0.1-10.0 mg/ml |
| Sodium Chloride | 2.0-10.0 mg/ml |
| Sodium Hydroxide | q.s. |
| Citric Acid | q.s. |
| Water | q.s. |

Example 4 is a prophetic example of a formulation comprising the vasodilator epoprostenol. Sodium chloride may be added to the solution to adjust tonicity, and sodium hydroxide and citric acid are added to adjust the pH of the solution. The solution of Example 4 may be made by methods known to those of ordinary skill in the art.

The Figures and attachments herein are presented for illustrative purposes only. They are not intended to limit the scope of the invention. Further, it should be understood that various changes and modifications to the embodiment described herein will be apparent to those skilled in the art. Such changes and modifications can be made without departing from the spirit and scope of the present invention and without diminishing its attendant advantages. It is therefore intended that such changes and modifications be covered by the appended claims. Also, the invention may suitably comprise, consist of or consist essentially of the elements or steps described herein. Further, the invention described herein suitably may comprise or be practiced in the absence of any element or step which is not specifically disclosed herein. Further, one or more step described herein may be performed simultaneously with another step.

That which is claimed:

1. An inhalable formulation for the treatment of pulmonary hypertension, said formulation consisting essentially of about 0.001 mg/ml to about 0.5 mg/ml of a hypertension reducing agent, a complexing agent, and about 0.001% to about 10% by weight emulsifying agent, said hypertension reducing agent consists of a calcium-channel blocker, said formulation is adapted for localized delivery to the lungs of a mammal via oral inhalation such that the formulation is deposited into the lungs of a patient and absorption of the hypertension reducing agent into the systemic blood circulation is less than the absorption of the hypertension reducing agent into the systemic blood circulation when administered intravenously or orally to the gastrointestinal tract and systemic side-effects associated with the hypertension reducing agent are less than the systemic side-effects realized when administered intravenously or orally to the gastrointestinal tract, said formulation is isotonic and has a pH of about 3 to about 8, said formulation is free of a preservative yet sterile and exhibits greater than 80% of the calcium-channel blocker originally present in the formulation after storage for 12 months at a temperature between 15 to 30° C., and said complexing agent is sodium edetate.

2. The formulation of claim 1, wherein said formulation is adapted for localized delivery to the lungs of a mammal by oral inhalation via nebulization.

3. The formulation of claim 2, further comprising a buffer.

4. The formulation of claim 2, wherein said formulation is an aqueous suspension.

5. The formulation of claim 2, wherein said calcium-channel blocker is at least one of the group consisting of amlodipine, bepridil, diltiazem, felodipine, flunarizine, isradipine, nicardipine, nifedipine, nimodipine and verapamil.

6. The formulation of claim 2, wherein said formulation is suitable for treating primary pulmonary hypertension.

7. The formulation of claim 2, wherein said formulation is suitable for treating secondary pulmonary hypertension.

8. An inhalable formulation for the treatment of pulmonary hypertension, said formulation consisting essentially of an aqueous suspension comprising: (a) 0.005 mg of a calcium-channel blocker; (b) 0.05 mg/ml of sodium edetate, (c) 0.001 to 5% by weight of a humectant consisting of sorbitol; and (d) about 0.001% to about 10% by weight emulsifying agent; and a pH of about 3 to about 4, wherein said formulation is adapted for localized delivery to the lungs of a mammal via oral inhalation such that the absorption of the calcium-channel blocker into the systemic blood circulation is less than the absorption of the hypertension reducing agent into the systemic blood circulation when administered intravenously or orally to the gastrointestinal tract and systemic side effects associated with the hypertension reducing agent are less than the systemic side-effects realized when administered intravenously or orally to the gastrointestinal tract; wherein said formulation is sterile and BAC-free and is provided in a pre-mixed, pre-measured, and unit dose form having a fill volume of from 0.1 to 1.5 ml; and wherein said formulation is free of a preservative yet sterile and exhibits greater than 80% of the calcium-channel blocker originally present in the formulation after storage for 12 months at a temperature between 15 to 30° C.

9. The formulation of claim 1, further comprising from 0.001 to 5% by weight of a humectant consisting of sorbitol.

10. The formulation of claim 1, wherein the complexing agent is selected from the group consisting of ethylenediaminetertraacetic acid, nitrilotriacetic acid, and salts thereof.

11. The formulation of claim 1, wherein said formulation is provided in a pre-mixed, pre-measured, and unit dose form having a fill volume of from 0.1 to 2.0 ml.

12. The formulation of claim 1, wherein said formulation is provided in a pre-mixed, pre-measured, and unit dose form having a fill volume of from 0.1 to 1.5 ml.

13. The formulation of claim 1, wherein said emulsifying agent comprises polyoxyethylene sorbitan fatty esters.

14. The formulation of claim 1, wherein said emulsifying agent comprises sorbitan trioleate.

15. The formulation of claim 1, wherein said formulation is BAC-free.

16. An inhalable formulation for the treatment of pulmonary hypertension, said formulation consisting essentially of about 0.001 mg/ml to about 0.5 mg/ml of a hypertension reducing agent, a complexing agent, and about 0.001% to about 10% by weight emulsifying agent, said hypertension reducing agent consists of a calcium-channel blocker, wherein said formulation is adapted for localized delivery to the lungs of a mammal via oral inhalation such that the formulation is deposited into the lungs of a patient and absorption of the hypertension reducing agent into the systemic blood circulation is less than the absorption of the hypertension reducing agent into the systemic blood circulation when administered intravenously or orally to the gastrointestinal tract and systemic side-effects associated with the hypertension reducing agent are less than the systemic side-effects realized when administered intravenously or orally to the gastrointestinal tract, said formulation is isotonic and has a pH of about 3 to about 8 and wherein said formulation is free of a preservative yet sterile and exhibits greater than 80% of the calcium-channel blocker originally present in the formulation after storage for 12 months at a temperature between 15 to 30° C., wherein said calcium-channel blocker comprises isradipine.

17. The formulation of claim 1, further comprising a tonicity agent comprising zinc chloride.

* * * * *

UNITED STATES PATENT AND TRADEMARK OFFICE
CERTIFICATE OF CORRECTION

PATENT NO. : 9,498,437 B2  
APPLICATION NO. : 11/316458  
DATED : November 22, 2016  
INVENTOR(S) : Imtiaz Chaudry Page 1 of 1

It is certified that error appears in the above-identified patent and that said Letters Patent is hereby corrected as shown below:

On the Title Page

"(63) Related U.S. Application Data:
Continuation of application No. PCT/EP2004/006629, filed on Jun. 18, 2004, which is a continuation of application No. 10/609,233, filed on June 27, 2003."

Should read:
--(63) Related U.S. Application Data:
Continuation of application No. PCT/EP2004/006629, filed on Jun. 18, 2004, and a Continuation of application US Application 10/609,233, filed on June 27, 2003.--

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*